United States Patent [19]

Lawson et al.

[11] Patent Number: 5,367,101

[45] Date of Patent: * Nov. 22, 1994

[54] PENTENE ISOMERIZATION PROCESS

[75] Inventors: Randy J. Lawson, Palatine; Dorothy M. Richmond, La Grange Park; Gregory J. Gajda, Mt. Prospect; Paul T. Barger, Arlington Heights, all of Ill.

[73] Assignee: UOP, Des Plaines, Ill.

[*] Notice: The portion of the term of this patent subsequent to Jul. 21, 2009 has been disclaimed.

[21] Appl. No.: 995,455

[22] Filed: Dec. 22, 1992

Related U.S. Application Data

[63] Continuation-in-part of Ser. No. 814,167, Dec. 30, 1991, Pat. No. 5,191,146, which is a continuation-in-part of Ser. No. 670,139, Mar. 15, 1991, Pat. No. 5,132,484, which is a continuation-in-part of Ser. No. 442,879, Nov. 29, 1989, abandoned.

[51] Int. Cl.$^5$ ............................ C07C 5/23; C07C 5/22; C07C 5/25
[52] U.S. Cl. ..................................... 585/667; 585/670; 585/671
[58] Field of Search ........................ 585/667, 670, 671

[56] References Cited

U.S. PATENT DOCUMENTS

| | | |
|---|---|---|
| 2,537,283 | 1/1951 | Schaad . |
| 3,211,801 | 10/1965 | Holm et al. . |
| 3,270,085 | 8/1966 | Noddings et al. . |
| 3,304,343 | 2/1967 | Mitsutani . |
| 3,327,014 | 1/1968 | Noddings et al. . |
| 3,448,164 | 6/1969 | Holm et al. . |
| 3,723,564 | 3/1973 | Tidwell et al. . |
| 3,751,502 | 8/1973 | Hayes et al. . |
| 3,800,003 | 3/1974 | Sobel . |
| 3,972,832 | 8/1976 | Butler et al. . |
| 4,440,871 | 4/1984 | Lok et al. ............................ 502/214 |
| 4,503,282 | 3/1985 | Sikkenga ............................ 585/671 |
| 4,554,143 | 11/1985 | Messina et al. ...................... 423/306 |
| 4,567,029 | 1/1986 | Wilson et al. ........................ 423/306 |
| 4,593,146 | 6/1986 | Johnson et al. ...................... 585/667 |
| 4,689,138 | 8/1987 | Miller ................................ 208/111 |
| 4,740,650 | 4/1988 | Pellet et al. ........................ 585/480 |
| 4,882,038 | 11/1989 | Lok et al. ............................ 208/111 |
| 5,107,050 | 4/1992 | Gaffney et al. ...................... 585/671 |
| 5,132,467 | 7/1992 | Haag et al. ........................... 568/697 |
| 5,132,484 | 7/1992 | Gajda ................................. 585/667 |
| 5,136,108 | 8/1992 | Gaffney et al. ...................... 568/697 |
| 5,191,146 | 3/1993 | Gajda et al. ......................... 585/667 |

Primary Examiner—Helen M. S. Sneed
Assistant Examiner—E. D. Irzinski
Attorney, Agent, or Firm—Thomas K. McBride; John F. Spears, Jr.; Richard E. Conser

[57] ABSTRACT

An improved process is disclosed for the isomerization of pentenes in the absence of hydrogen using a catalyst comprising a non-zeolitic molecular sieve. It is of particular interest to increase the proportion of olefins containing tertiary carbons in the product with low formation of undesirable by-products. Product olefins may be further processed to obtain methyl t-amyl ether, which enjoy high current interest as components for reformulated gasoline. Pentenes in raffinate from etherification may be returned to the isomerization process.

17 Claims, 4 Drawing Sheets

PENTENE ISOMERIZATION PROCESS

CROSS REFERENCE TO RELATED APPLICATION

This application is a continuation-in-part of prior copending application Ser. No. 814,167, filed on Dec. 30, 1991 and now U.S. Pat. No. 5,191,146 which is a continuation-in-part of application Ser. No. 670,139, filed Mar. 15, 1991 and now U.S. Pat. No. 5,132,484, which is a continuation-in-part of application Ser. No. 442,879, filed Nov. 29, 1989 and now abandoned, the contents of all of which are incorporated herein by reference thereto.

BACKGROUND OF THE INVENTION

1. Field of the Invention

This invention relates to an improved process for the conversion of hydrocarbons, and more specifically for the catalytic isomerization of olefinic hydrocarbons.

2. General Background Olefinic hydrocarbons are feedstocks for a variety of commercially important addition reactions to yield fuels, polymers, oxygenates and other chemical products. The specific olefin isomer, considering the position of the double bond or the degree of branching of the hydrocarbon, may be important to the efficiency of the chemical reaction or to the properties of the product. The distribution of isomers in a mixture of olefinic hydrocarbons is rarely optimum for a specific application. It is often desirable to isomerize olefins to increase the output of the desired isomer.

Butenes are among the most useful of the olefinic hydrocarbons having more than one isomer. A high-octane gasoline component is produced from a mixture of butenes in many petroleum refineries principally by alkylation with isobutane; 2-butenes (cis- and trans-) generally are the most desirable isomers for this application. Secondary-butyl alcohol and methylethyl ketone, as well as butadiene, are other important derivatives of 2-butenes. Demand for 1-butene has been growing rapidly based on its use as a comonomer for linear low-density polyethylene and as a monomer in polybutene production. Isobutene finds application in such products as methyl methacrylate, polyisobutene and butyl rubber. The most important derivative influencing isobutene demand and butene isomer requirements, however, is methyl t-butyl ether (MTBE) which is experiencing rapid growth in demand as a gasoline component.

Pentenes also are valuable olefinic feedstocks for fuel and chemical products. Isoprene, which may be produced by dehydrogenation of isopentene, is an important monomer in the production of elastomers. To an increasing extent, pentenes obtained from refinery cracking units are alkylated with isobutane to obtain a high-octane gasoline component. The principal influence on trends in isopentene demand and pentene isomer requirements, however, is the rapid growth in demand for methyl t-amyl ether (TAME) as a gasoline component. This derivative is of increasing interest as restrictions on gasoline olefins and volatility reduce the utility of pentenes as a gasoline component and as ethers and alcohols are needed for reformulated gasolines with higher oxygen content. This interest may extend to hexenes and higher olefins having tertiary carbons which could be reacted to yield high-octane ethers.

Olefin isomers rarely are obtained in a refinery or petrochemical product in a ratio matching product demand. In particular, there is a widespread need to increase the proportion of isobutene, isopentene and other tertiary-carbon olefins for production of MTBE, TAME and other ethers. Catalytic isomerization to alter the ratio of isomers is one solution to this need. Since ethers must be supplied at lower cost to find widespread use as a fuel product and since isomerization competes with increased feedstock processing as a source of desired isomers, an isomerization process must be efficient and relatively inexpensive. In one aspect, a catalytic isomerization process must recognize olefin reactivity: isobutene in particular readily forms oligomers which could require a reconversion step to yield monomer if produced in excess. The principal problem facing workers in the art therefore is to isomerize olefins to increase the concentration of the desired isomer while minimizing product losses to heavier or lighter products.

3. Related Art

Processes for the isomerization of olefinic hydrocarbons are widely known in the art. Many of these use catalysts comprising phosphate. U.S. Pat. No. 2,537,283 (Schaad), for example, teaches an isomerization process using an ammonium phosphate catalyst and discloses examples of butene and pentene isomerization. U.S. Pat. No. 3,211,801 (Holm et al.) discloses a method of preparing a catalyst comprising precipitated aluminum phosphate within a silica gel network and the use of this catalyst in the isomerization of butene-1 to butene-2. U.S. Pat. Nos. 3,270,085 and 3,327,014 (Noddings et al.) teach an olefin isomerization process using a chromium-nickel phosphate catalyst, effective for isomerizing 1-butene and higher alpha-olefins. U.S. Pat. No. 3,304,343 (Mitsutani) reveals a process for double-bond transfer based on a catalyst of solid phosphoric acid on silica, and demonstrates effective results in isomerizing 1-butene to 2-butenes. U.S. Pat. No. 3,448,164 (Holm et al.) teaches skeletal isomerization of olefins to yield branched isomers using a catalyst containing aluminum phosphate and titanium compounds. U.S. Pat. No. 4,593,146 teaches isomerization of an aliphatic olefin, preferably 1-butene, with a catalyst consisting essentially of chromium and amorphous aluminum phosphate. None of the above references disclose the olefin-isomerization process using the non-zeolitic molecular sieve (NZMS) of the present invention.

The art also contains references to the related use of zeolitic molecular sieves. U.S. Pat. No. 3,723,564 (Tidwell et al.) teaches the isomerization of 1butene to 2-butene using a zeolitic molecular sieve. U.S. Pat. No. 3,751,502 (Hayes et al.) discloses the isomerization of mono-olefins based on a catalyst comprising crystalline aluminosilicate in an alumina carrier with platinum-group and Group IV-A metallic components. U.S. Pat. No. 3,800,003 (Sobel) discloses the employment of a zeolite catalyst for butene isomerization. U.S. Pat. No. 3,972,832 (Butler et al.) teaches the use of a phosphorus-containing zeolite, in which the phosphorus has not been substituted for silicon or aluminum in the framework, for butene conversion. None of the above teach the use of NZMS for selective butene isomerization, and Butler et al. discloses high yields of heavier olefins from butenes at a range of temperatures with a phosphorus-containing zeolite.

U.S. Pat. No. 4,503,282 (Sikkenga) reveals a process for converting linear alkenes to isomerized alkenes using a crystalline borosilicate molecular sieve, with examples demonstrating the conversion of linear butenes to isobutene. U.S. Pat. No. 5,132,467 (Haag et al.), filed Mar. 6, 1991, teaches a combination of two-stage etherification followed by common fractionation and olefin isomerization; the isomerization is carried out over a medium-pore metallosilicate catalyst with a range of ZSMs and MCM-22 being disclosed. The isomerization of olefins using NZMS, containing tetrahedral aluminum, phosphorus and at least one other element, has not been disclosed in the above references.

U.S. Pat. No. 5,107,050 (Gaffney et al.), filed Dec. 28, 1990, discloses butene isomerization using a MgAPSO or SAPO molecular sieve at a temperature above 900° F. U.S. Pat. No. 5,136,108 (Gaffney et al.), filed Mar. 6, 1991, teaches a combination process for producing TAME and/or TAA by reacting tertiary pentenes with methanol and/or water, distillation to separate reactants, and isomerization of $C_5$ hydrocarbons with return of branched hydrocarbons to TAME/TAA production; preferred isomerization catalysts are SAPOs and MgAPSOs.

"Non-zeolitic molecular sieves" or "NZMSs" as referenced herein include the "SAPO" silicoaluminophosphates of U.S. Pat. No. 4,440,871 (Lok et al.), the "FAPO" ferroaluminophosphates of U.S. Pat. No. 4,554,143 (Messina et al.), and the metal aluminophosphates of U.S. Pat. No. 4,567,029 (Wilson et al.) wherein the metal is at least one of Mn, Co, Zn and Mg. The application of NZMS-containing catalyst to the isomerization of a $C_8$ aromatics stream is revealed in U.S. Pat. No. 4,740,650 (Pellet et al.). U.S. Pat. No. 4,689,138 teaches a process for isomerizing normal and slightly branched paraffins using a catalyst comprising SAPO molecular sieves. The use of MgAPSO compositions for hydrocarbon conversion is taught in U.S. Pat. No. 4,882,038. However, none of these references discloses or suggests the isomerization of olefins using a catalyst containing NZMS and having the absence of a hydrogenation promoter.

SUMMARY OF THE INVENTION

Objects

It is an object of the present invention to provide an improved process for the isomerization of olefinic hydrocarbons. A corollary objective of the invention is to minimize product losses from an olefin isomerization process.

Summary

This invention is based on the discovery that a catalytic isomerization process using a catalyst comprising at least one NZMS and having the absence of a platinum-group metal demonstrates surprising efficiency in converting 2-butene to isobutene or 1-butene in a butene-isomerization operation and in the skeletal isomerization of pentenes.

Embodiments

A broad embodiment of the present invention is directed to the catalytic isomerization of olefinic hydrocarbons using a catalyst containing at least one NZMS and having the absence of a hydrogenation promoter.

In a preferred embodiment, the feedstock to catalytic isomerization comprises principally butenes. In a highly preferred embodiment, the catalytic isomerization increases the concentration of isobutene in the product. An alternative preferred embodiment comprises the isomerization of linear pentenes to isopentene. Optionally, the isomerization is carried out in the substantial absence of hydrogen.

In another aspect, the NZMS of the catalyst comprises silicoaluminophosphates or" SAPO." In an alternative embodiment, the catalyst comprises a MgAPSO sieve.

These as well as other objects and embodiments will become apparent from the detailed description of the invention.

DESCRIPTION OF THE PREFERRED EMBODIMENTS

To reiterate, a broad embodiment of the present invention is directed to the catalytic isomerization of olefinic hydrocarbons using a catalyst containing at least one NZMS.

Process

According to the process of the present invention, an olefinic hydrocarbon charge stock is contacted with a catalyst containing at least one NZMS in a hydrocarbon isomerization zone. Contacting may be effected using the catalyst in a fixed-bed system, a moving-bed system, a fluidized-bed system, or in a batch-type operation. In view of the potential attrition loss of the valuable catalyst and of the operational advantages, a fixed-bed system is preferred. The conversion zone may be in one reactor or in separate reactors with suitable means therebetween to ensure that the desired isomerization temperature is maintained at the entrance to each reactor. The reactants may contact the catalyst in the liquid phase, a mixed vapor-liquid phase, or a vapor phase. Preferably, the reactants contact the catalyst in the vapor phase. The contact may be effected in each reactor in either an upward, downward, or radial-flow manner.

The charge stock may contact the catalyst in the absence of hydrogen or in presence of hydrogen in a molar ratio to charge stock of from about 0.01 to about 10. Hydrogen may be supplied totally from outside the isomerization process, or the outside hydrogen may be supplemented by hydrogen separated from reaction products and recycled to the charge stock. Inert diluents such as nitrogen, argon, methane, ethane and the like may be present. Although the principal isomerization reaction does not consume hydrogen, there may be net consumption of hydrogen in such side reactions as cracking and olefin saturation. In addition, hydrogen may suppress the formation of carbonaceous compounds on the catalyst and enhance catalyst stability.

A stable operation may be maintained within the above parameters as noted in the substantial absence of hydrogen, particularly when isomerizing pentenes. "Absence of hydrogen" means that free or molecular hydrogen is substantially absent in the feed to the present catalyst. Nitrogen or other inert gases may be used for plant pressurization. Hydrogen is considered to be substantially absent at a level below the saturation level in the hydrocarbon feedstock, more usually at a level of about 0.0.05 or lower molar ratio to the feedstock, and especially at a molar ratio to the feedstock of about 0.001 or less.

In the group of olefinic hydrocarbons suitable as feedstock to the catalytic isomerization process of the present invention, mono-olefins having from 4 to 10 carbon atoms per molecule are preferred. The mono-olefins should be present in the feedstock in a concentration of from about 0.5 to 100 mass %, and preferably from about 5 to 100 mass %, with most of the balance usually comprising paraffins. Butenes are an especially preferred feedstock. The feedstock should be rich in one or more of the linear butenes, i.e., 1-butene, cis-2-butene and trans-2-butene, if isobutene is the desired product.

An advantageous alternative feedstock within the group of preferred olefins comprises pentenes, often designated amylenes. Optimally one or both of the linear pentenes 1-pentene and 2-pentene are isomerized to one or more of the isopentenes 2-methyl-2-butene, 2-methyl-1-butene, and 3-methyl-1-butene. A pentene-containing feedstock also may contain hexenes and, optionally, higher olefins.

The feedstock olefins may be contained in product streams from petroleum-refining, synthetic-fuel, or petrochemical operations such as catalytic cracking, thermal cracking, stream pyrolysis, oligomerization, and Fischer-Tropsch synthesis. Often the feedstock contains paraffins such as butanes, pentanes, and $C_6$ and higher paraffins. An advantageous feedstock for isobutene or isopentene production is raffinate from an etherification process. The derivation of the feedstock from an etherification process is well known and is described, inter alia, in a paper by Bruno Notari, et al., "Skeletal Isomerization of Olefins," at the 1980 NPRA Annual Meeting in New Orleans on Mar. 23-25, 1980.

These streams may require removal of polar contaminants such as sulfur, nitrogen or oxygen compounds by, e.g., extraction or adsorption to maintain isomerization-catalyst stability. Raffinate from an etherification process would beneficially be water-washed to remove methanol and other oxygenates present at levels which could affect the performance of the present catalyst. Removal of dienes and acetylenes, e.g., by selective hydrogenation or polymerization, also may be desirable.

In an alternative embodiment, from about 10 to 300 mass ppm of an organic chloride promoter may be added to the charge stock.

Isomerization conditions include reaction temperatures generally in the range of about 50° to 750° C. For the isomerization of butenes to increase the concentration of isobutene temperatures in the range of 200° to 600° C., and especially 250° to 400° C., are preferred. Selective butene isomerization to produce 1-butene is effected preferably at temperatures of from 50° to 300° C. Pentene isomerization is advantageously performed at temperatures in the range of about 200° to 500° C. Reactor operating pressures usually will range from about atmospheric to 50 atmospheres. The amount of catalyst in the reactors will provide an overall weight hourly space velocity of from about 0.5 to 100 hr$^{-1}$, and preferably from about 1 to 40 hr$^{-1}$.

The particular product-recovery scheme employed is not deemed to be critical to the present invention; any recovery scheme known in the art may be used. Typically, the reactor effluent will be condensed and the hydrogen and inerts removed therefrom by flash separation. The condensed liquid product then is fractionated to remove light materials from the liquid product. The selected isomer, e.g., isobutene or 1-butene or the isopentene isomer mixture, may be separated from the liquid product by adsorption, fractionation, extraction or reaction. A preferred reaction for separation of either isobutene or isopentene is etherification for production of methyl or ethyl t-butyl ether or for methyl t-amyl ether, respectively. Production of ethers from tertiary olefins is known in the art and described, inter alia, in J. D. Chase, et al., "MTBE and TAME—a Good Octane Boosting Combo," *Oil and Gas Journal*, Apr. 9, 1979, pp. 149-152. The raffinate from the separation step may be returned to the isomerization zone for futher conversion to the selected isomer. The combination of olefin isomerization and etherification in a process combination has been widely disclosed, e.g., in a paper by Bruno Notari, et al., "Skeletal Isomerization of Olefins," at the 1980 NPRA Annual Meeting in New Orleans on Mar. 23-25, 1980, U.S. Pat. Nos. 3,979,461 (Ancillotti et al.) and 4,554,386 (Groenveld et al.), and French Publication 2 614 297 (Gaillard et al.), incorporated herein by reference for disclosure of the state of the art of the isomerization/etherification combination.

Catalyst

An essential component of the catalyst of the present invention is at least one non-zeolitic molecular sieve, also characterized as "NZMS" and defined in the instant invention to include molecular sieves containing framework tetrahedral units (TO$_2$) of aluminum (AlO$_2$), phosphorus (PO$_2$) and at least one additional element (EL) as a framework tetrahedral unit (ELO$_2$). "NZMS" includes the "SAPO" molecular sieves of U.S. Pat. No. 4,440,871, "ELAPSO" molecular sieves as disclosed in U.S. Pat. No. 4,793,984 and certain "MeAPO", "FAPO", "TAPO" and "MAPO" molecular sieves, as hereinafter described. Crystalline metal aluminophosphates (MeAPOs where "Me" is at least one of Mg, Mn, Co and Zn) are disclosed in U.S. Pat. No. No. 4,567,029, crystalline ferroaluminophosphates (FAPOs) are disclosed in U.S. Pat. No. 4,554,143, titanium aluminophosphates (TAPOs) are disclosed in U.S. Pat. No. No. 4,500,651, MAPO metal aluminophosphates wherein M is As, Be, B, Cr, Ga, Ge, Li or V are disclosed in U.S. Pat. No. 4,686,093, and binary metal aluminophosphates are described in Canadian Patent 1,241,943. ELAPSO molecular sieves also are disclosed in patents drawn to species thereof, including but not limited to GaAPSO as disclosed in U.S. Pat. No. 4,735,806, BeAPSO as disclosed in U.S. Pat. No. 4,737,353, CrAPSO as disclosed in U.S. Pat. No. 4,738,837, CoAPSO as disclosed in U.S. Pat. No. 4,744,970, MgAPSO as disclosed in U.S. Pat. No. 4,758,419 and MnAPSO as disclosed in U.S. Pat. No. 4,793,833. The aforementioned patents are incorporated herein by reference thereto. The nomenclature employed herein to refer to the members of the aforementioned NZMSs is consistent with that employed in the aforementioned applications or patents. A particular member of a class is generally referred to as a "-n" species wherein "n" is an integer, e.g., SAPO-11, MeAPO-11 and ELAPSO-31. In the following discussion on NZMSs set forth hereinafter the mole fraction of the NZMS are defined as compositional values which are plotted in phase diagrams in each of the identified patents, published applications or copending applications.

The preferred NZMSs are the silicoaluminophosphate molecular sieves described in U.S. Pat. No. 4,440,871. The silicoaluminophosphate molecular sieves are disclosed as microporous crystalline silicoaluminophosphates, having a three-dimensional microporous framework structure of $PO_2^+$, $AlO_2^-$ and $SiO_2$ tetrahedral units, and whose essential empirical chemical composition on an anhydrous basis is:

wherein "R" represents at least one organic templating agent present in the intracrystalline pore system; "m" represents the moles of "R" present per mole of $(Si_xAl_yP_z)O_2$ and has a value of from 0.02 to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 1 of U.S. Pat. No. 4,440,871, and represent the following values for "x", "y" and "z":

| Point | Mole Fraction | | |
|-------|------|------|------|
|  | x | y | z |
| A | 0.01 | 0.47 | 0.52 |
| B | 0.94 | 0.01 | 0.05 |
| C | 0.98 | 0.01 | 0.01 |
| D | 0.39 | 0.60 | 0.01 |
| E | 0.01 | 0.60 | 0.39 |

The silicoaluminophosphates of U.S. Pat. No. No. 4,440,871 are generally referred to therein as "SAPO" as a class, or as "SAPO-n" wherein "n" is an integer denoting a particular SAPO such as SAPO-11, SAPO-31, SAPO-40 and SAPO-41. The especially preferred species SAPO-11 as referred to herein is a silicoaluminophosphate having a characteristic X-ray powder diffraction pattern which contains at least the d-spacings set forth below:

| SAPO-11 | | |
|------|------|------|
| 2r | d | Relative Intensity |
| 9.4–9.65 | 9.41–9.17 | m |
| 20.3–20.6 | 4.37–4.31 | m |
| 21.0–21.3 | 4.23–4.17 | vs |
| 21.1–22.35 | 4.02–3.99 | m |
| 22.5–22.9 (doublet) | 3.95–3.92 | m |
| 23.15–23.35 | 3.84–3.81 | m–s |

Ferroaluminophosphates are disclosed in U.S. Pat. No. 4,554,143, incorporated herein by reference, and have a three-dimensional microporous crystal framework structure of $AlO_2$, $FeO_2$, and $PO_2$ tetrahedral units and have an essential empirical chemical composition, on an anhydrous basis, of:

wherein "R" represents at least one organic templating agent present in the intracrystalline pore system; "m" represents the moles of "R" present per mole of $(Fe_xAl_yP_z)O_2$ and has a value of from zero to 0.3, the maximum value in each case depending upon the molecular dimensions of the templating agent and the available void volume of the pore system of the particular ferroaluminophosphate involved; "x", "y", and "z" represent the mole fractions of iron, aluminum and phosphorus, respectively, present as tetrahedral oxides, representing the following values for "x", "y", and "z":

| Point | Mole Fraction | | |
|-------|------|------|------|
|  | x | y | z |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02. The iron of the $FeO_2$ structural units can be in either the ferric or ferrous valence state, depending largely upon the source of the iron in the synthesis gel. Thus, an $FeO_2$ tetrahedron in the structure can have a net charge of either $-1$ or $-2$. While it is believed that the Fe, Al and P framework constituents are present in tetrahedral coordination with oxygen (and are referred to herein as such), it is theoretically possible that some minor fraction of these framework constituents are present in coordination with five or six oxygen atoms. It is not, moreover, necessarily the case that all of the Fe, Al and/or P content of any given synthesized product is a part of the framework in the aforesaid types of coordination with oxygen. Some of each constituent may be merely occluded or in an yet undetermined form and may or may not be structurally significant.

For convenience in describing the ferroaluminophosphates, the "shorthand" acronym "FAPO" is sometimes employed hereinafter. To identify the various structural species which make up the generic class FAPO, each species is assigned a number and is identified, for example, as FAPO-11, FAPO-31 and so forth.

MeAPO molecular sieves are crystalline microporous aluminophosphates in which the substituent metal is one of a mixture of two or more divalent metals of the group magnesium, manganese, zinc and cobalt and are disclosed in U.S. Pat. No. 4,567,029. Members of this novel class of compositions have a three-dimensional microporous crystal framework structure of $MO_2^{-2}$, $AlO_2^-$ and $PO_2^+$ tetrahedral units and have an essential empirical chemical composition, on an anhydrous basis, of:

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved; "x", "y", and "z" represent the mole fractions of the metal "M", (i.e., magnesium, manganese, zinc and cobalt), aluminum and phosphorus, respectively, present as tetrahedral oxides, said mole fractions being such that they are within the following limiting values for "x", "y", and "z":

| Point | Mole Fraction | | |
|---|---|---|---|
| | x | y | z |
| A | 0.01 | 0.60 | 0.39 |
| B | 0.01 | 0.39 | 0.60 |
| C | 0.35 | 0.05 | 0.60 |
| D | 0.35 | 0.60 | 0.05 |

When synthesized the minimum value of "m" in the formula above is 0.02.

The CoAPSO molecular sieves of U.S. Pat. No. 4,744,970 have three-dimensional microporous framework structures of $CoO_2^{-2}$, $AlO_2^-$, $PO_2^+$ and $SiO_2$ tetrahedral units and have an empirical chemical composition on an anhydrous basis expressed by the formula:

$$mR:(Co_wAl_xP_ySi_z)O_2$$

wherein "R" represents at least one organic templating agent present in the intracrystalline pore system; "m" represents the molar amount of "R" present per mole of $(Co_wAl_xP_ySi_z)O_2$ and has a value of from zero to about 0.3; and "w", "x", "y" and "z" represent the mole fractions of cobalt, aluminum, phosphorus and silicon, respectively, present as tetrahedral oxides, where the mole fractions "w", "x", "y" and "z" are each at least 0.01 and are generally defined, as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

The MgAPSO molecular sieves of U.S. Pat. No. 4,758,419 have a framework structure of $MgO_2^{-2}$, $AlO_2^-$, $PO_2^+$, and $SiO_2$ tetrahedral units having an empirical chemical composition on an anhydrous basis expressed by the formula:

$$mR:(Mg_wAl_xP_ySi_z)O_2$$

wherein "R" represents at least one organic templating agent present in the intracrystalline pore system; "m" represents the molar amount of "R" present per mole of $(Mg_wAl_xP_ySi_z)O_2$ and has a value of zero to about 0.3; and "w", "x", "y" and "z" represent the mole fractions of elemental magnesium, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

The MnAPSO molecular sieves of U.S. Pat. No. 4,793,833 have a framework structure of $MnO_2^{-2}$, $AlO_2^-$, $PO_2^+$, and $SiO_2$ tetrahedral units having an empirical chemical composition on an anhydrous basis expressed by the formula:

$$mR:(Mn_wAl_xP_ySi_z)O_2$$

wherein "R" represents at least one organic templating agent present in the intracrystalline pore system; "m" represents the molar amount of "R" present per mole of $(Mn_wAl_xP_ySi_z)O_2$ and has a value of zero to about 0.3; and "w", "x", "y" and "z" represent the mole fractions of element manganese, aluminum, phosphorus and silicon, respectively, present as tetrahedral oxides. The mole fractions "w", "x", "y" and "z" are generally defined as being within the limiting compositional values or points as follows:

| Point | Mole Fraction | | |
|---|---|---|---|
| | x | y | (z + w) |
| A | 0.60 | 0.38 | 0.02 |
| B | 0.38 | 0.60 | 0.02 |
| C | 0.01 | 0.60 | 0.39 |
| D | 0.01 | 0.01 | 0.98 |
| E | 0.60 | 0.01 | 0.39 |

It is within the scope of the invention that the catalyst comprises two or more NZMSs. Preferably the NZMSs are as a multi-compositional, multi-phase composite having contiguous phases, a common crystal framework structure and exhibiting a distinct heterogeneity in composition, especially wherein one phase comprises a deposition substrate upon which another phase is deposited as an outer layer. Such composites are described in U.S. Pat. No. 4,861,739, incorporated herein by reference thereto. In a highly preferred embodiment the layered catalyst comprises a crystalline aluminophosphate of U.S. Pat. No. 4,310,440 and a SAPO, especially ALPO-11 and SAPO-11.

The NZMS preferably is combined with a binder for convenient formation of catalyst particles. The binder should be porous, adsorptive support having a surface area of about 25 to about 500 m²/g, uniform in composition and relatively refractory to the conditions utilized in the hydrocarbon conversion process. By the term "uniform in composition," it is meant that the support be unlayered, have no concentration gradients of the species inherent to its composition, and be completely homogeneous in composition. Thus, if the support is a mixture of two or more refractory materials, the relative amounts of these materials will be constant and uniform throughout the entire support., It is intended to include within the scope of the present invention carrier materials which have traditionally been utilized in hydrocarbon conversion catalysts such as: (1) refractory inorganic oxides such as alumina, titanium dioxide, zirconium dioxide, chromium oxide, zinc oxide, magnesia, thoria, boria, silica-alumina, silica-magnesia, chromiaalumina, alumina-boria, silica-zirconia, etc.; (2) ceramics, porcelain, bauxite; (3) silica or silica gel, silicon carbide, clays and silicates including those synthetically prepared and naturally occurring, which may or may not be acid treated, for example attapulgus clay, diatomaceous earth, fuller's earth, kaolin, kieselguhr, etc.; (4) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations, (5) spinels such as $MgAl_2O_4$, $FeAl_2O_4$, $ZnAl_2O_4$, $CaAl_2O_4$, and other like compounds having the formula $MOAl_2O_3$ where M is a metal having a valence of 2; and (6) combinations of materials from one or more of these groups.

The preferred binder to effect a selective finished catalyst is a form of amorphous silica. The preferred amorphous silica is a synthetic, white, amorphous silica (silicon dioxide) powder which is classed as wet-process, hydrated silica. This type of silica is produced by a chemical reaction in a water solution, from which it is precipitated as ultra-fine, spherical particles. It is preferred that the BET surface area of the silica is in the range from about 120 to 160 $m^2/g$. A low content of sulfate salts is desired, preferably less than 0.3 wt. %. It is especially preferred that the amorphous silica binder be nonacidic, e.g., that the pH of a 5% water suspension be neutral or basic (pH about 7 or above).

NZMS and binder are combined to form an extrudable dough, having the correct moisture content to allow for the formation of extrudates with acceptable integrity to withstand direct calcination. Extrudability is determined from an analysis of the moisture content of the dough, with a moisture content in the range of from 30 to 50 wt. % being preferred. Extrusion is performed in accordance with the techniques well known in the art. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by any means known to the art.

An optional component of the present catalyst is a platinum-group metal including one or more of platinum, palladium, rhodium, ruthenium, osmium, and iridium. Preferably the catalyst is substantially free of a hydrogenation promoter such as a Group VIII (8–10) or VIB (6) metal of the Periodic Table [See Cotton and Wilkinson, *Advanced Organic Chemistry*, John Wiley & Sons (Fifth Edition, 1988)] which would result in economically significant losses of olefins to paraffins through hydrogenation. The preferred catalyst contains less than 100 mass parts per million (ppm) on an elemental basis of hydrogenation promoter, and optimally less than about 10 mass ppm. It is especially preferred that the catalyst be substantially free of platinum and palladium.

The catalyst of the present invention may contain a halogen component. The halogen component may be either fluorine, chlorine, bromine or iodine or mixtures thereof. Chlorine is the preferred halogen component. The halogen component is generally present in a combined state with the inorganic-oxide support. The halogen component is preferably well dispersed throughout the catalyst and may comprise from more than 0.2 to about 15 wt. %, calculated on an elemental basis, of the final catalyst.

The optional halogen component may be incorporated in the catalyst in any suitable manner, either during the preparation of the inorganic-oxide support or before, while or after other catalytic components are incorporated. For example, the carrier material may contain halogen and thus contribute at least some portion of the halogen content in the final catalyst. The halogen component or a portion thereof also may be added to the catalyst during the incorporation of other catalyst components into the support. Also, the halogen component or a portion thereof may be added to the catalyst by contacting with the halogen or a compound, solution, suspension or dispersion containing the halogen before or after other catalyst components are incorporated into the support. Suitable compounds containing the halogen include acids containing the halogen, e.g., hydrochloric acid. The halogen component or a portion thereof may be incorporated by contacting the catalyst with a compound, solution, suspension or dispersion containing the halogen in a subsequent catalyst regeneration step. The catalyst composite is dried at a temperature of from about 100° to about 320° C. for a period of from about 2 to about 24 or more hours and calcined at a temperature of from 400° to about 650° C. in an air atmosphere for a period of from about 0.1 to about 10 hours. The optional halogen component may be adjusted by including a halogen or halogen-containing compound in the air atmosphere.

EXAMPLES

The following examples are presented to demonstrate the present invention and to illustrate certain specific embodiments thereof. These examples should not be construed to limit the scope of the invention as set forth in the claims. There are many possible other variations, as those of ordinary skill in the art will recognize, which are within the spirit of the invention.

Example I

Example I illustrates the conversion of a feedstock rich in 2-butenes over a catalyst of the invention with reaction temperature as the principal variable. The composition of the feedstock was as follows in mass %:

| | |
|---|---|
| Butanes | 0.497 |
| Isobutene | 0.538 |
| 2-butenes | 94.747 |
| Heavy components | 4.217 |

Product yields are expressed as mass % of the total products. The approach to equilibrium butene-isomer distribution was determined by reference to equilibrium values calculated from free energies of formation contained in "Selected Values of Physical and Thermodynamic Properties of Hydrocarbons and Related Compounds," API Research Project 44 (1953). This approach to equilibrium is expressed for isomerization to isobutene in FIG. 1 as % of isobutene equilibrium relative to reaction temperature.

Catalysts were evaluated using a ½-inch stainless-steel tube as a micro-reactor. One gram of catalyst as powder was placed in the reactor. Butene-rich feedstock was charged to the reactor at its vapor pressure at 70° F. by a syringe pump. The reaction temperature was monitored by a thermocouple in the catalyst bed and controlled by heating the reactor in a fluidized sandbath.

Sandbath temperature was controlled by a thermocouple. The liquid products were analyzed by vapor-phase chromatography.

Catalyst performance was compared using a Figure of Merit, or FOM. FOM is obtained by multiplying the mass percent of desired product (isobutene or 1-butene) in the total reactor products by the ratio of (desired product)/(desired product plus light plus heavy by-products). The first term is a measure of conversion as well as selectivity, while the second term reflects selectivity. Thus, FOM is a measure of conversion and selectivity with an emphasis on selectivity. FOM is reported hereinbelow at the reactor temperature at which it reaches its maximum value for each of the catalysts.

The process of the present invention was demonstrated by effecting isomerization of 2-butene to isobutene over SAPO-11 catalyst. SAPO-11 catalyst is characterized as described hereinabove, and the specific catalyst samples used in these tests had the following approximate properties:

| Composition, mass %: | $Al_2O_3$ | 41.7 |
| --- | --- | --- |
| | $P_2O_5$ | 50.5 |
| | $SiO_2$ | 7.8 |
| | | 100.0 |

The 2-butene-rich feedstock described above was charged to the micro-reactor, operating at atmospheric pressure. Reaction temperature was increased in a series of steps, and two or more product analyses were performed at each temperature. The results shown below represent average results at each temperature:

| Temperature, °C. | 260° | 318° | 343° | 370° |
| --- | --- | --- | --- | --- |
| WHSV | 2.2 | 1.5 | 4.7 | 5.2 |
| Products, mass % | | | | |
| $C_3$ and lighter | 0.1 | 1.0 | 2.7 | 2.2 |
| Butanes | 2.5 | 2.8 | 3.5 | 2.8 |
| Isobutene | 9.6 | 13.2 | 26.7 | 23.4 |
| 1-butene | 15.8 | 13.2 | 11.8 | 11.1 |
| 2-butenes | 66.0 | 53.8 | 38.1 | 37.8 |
| $C_5$ and heavier | 6.0 | 16.0 | 17.2 | 22.7 |

Example II

A control of the prior art was developed to contrast with the process of the present invention. A zeolitic molecular-sieve catalyst was tested for the isomerization of 2-butene to isobutene. The catalyst had the following approximate characteristics:

| Composition, mass %: | $Al_2O_3$ | 4.3 |
| --- | --- | --- |
| | $SiO_2$ | 95.6 |
| | CaO | 0.1 |
| | | 100.0 |

Tests were performed and results measured using the feedstock and procedures of Example I. Results were as follows:

| Temperature, °C. | 261° | 290° | 317° |
| --- | --- | --- | --- |
| WHSV | 2.9 | 5.0 | 4.1 |
| Products, mass %: | | | |
| $C_3$ and lighter | 1.0 | 3.6 | 1.0 |
| Butanes | 0.9 | 2.0 | 0.5 |
| Isobutene | 1.1 | 3.0 | 1.2 |

-continued

| Temperature, °C. | 261° | 290° | 317° |
| --- | --- | --- | --- |
| 1-butene | 14.2 | 4.7 | 1.9 |
| 2-butenes | 74.5 | 16.5 | 7.4 |
| $C_5$ and heavier | 8.3 | 70.2 | 88.0 |

Temperatures were not increased above 320° C., as the proportion of isomerization became irrelevant due to the increasing predominance of the reaction forming heavy components.

Example III

Figure 1:
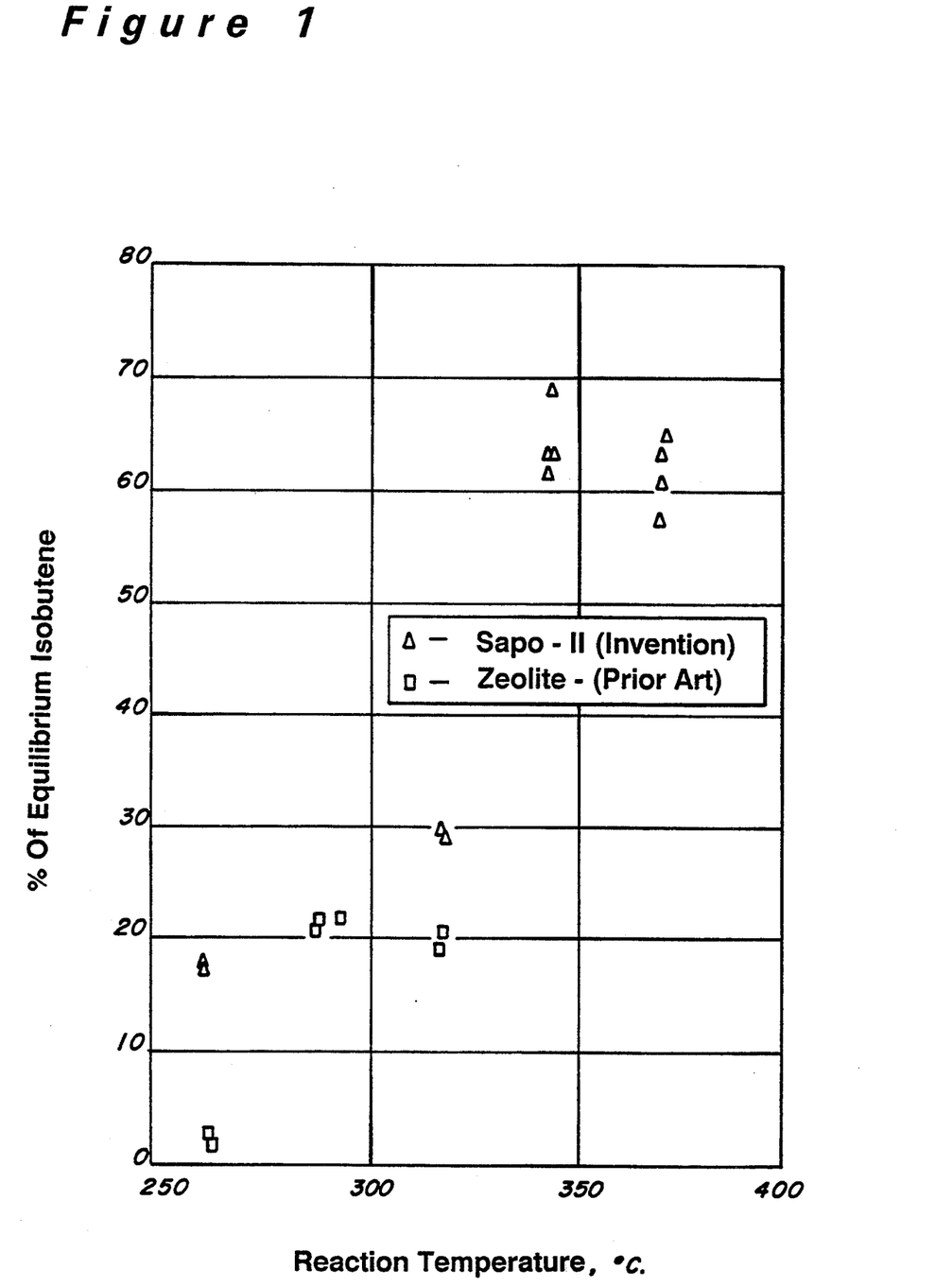
FIG. 1 shows the approach to equilibrium isobutene concentration in the reactor product, relative to reaction temperature, when employing catalysts of the invention and of the prior art. The proportion of isobutene relative to total butenes for each test was divided by the equilibrium proportion of isobutene, calculated from API Research Project 44, at the respective reaction temperature of the test.

The test results used to develop Examples I and II were compared with equilibrium isomer values based on the aforementioned API Research Project 44, and the results were plotted in FIG. 1. Data based on individual tests are shown in FIG. 1, whereas the tables of Examples I and II are based on averages of test results at substantially equivalent temperatures.

The process based on the catalyst of the invention achieves a substantially higher conversion to isobutene than the catalyst of the prior art. The equilibrium data understate the advantage of the present invention; due to the high yield of heavy product when using the prior-art catalyst.

Figure 2:
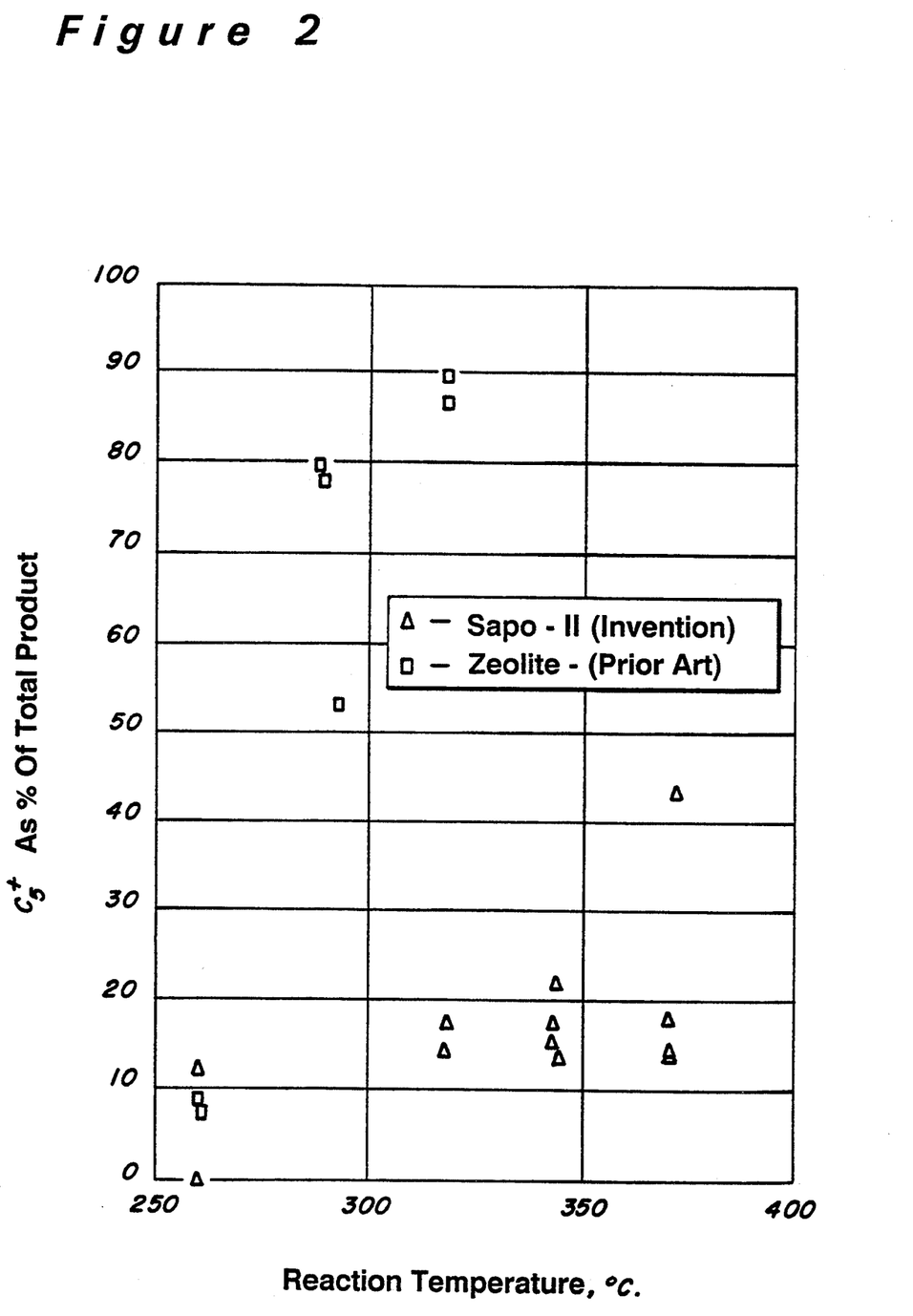
FIG. 2 shows the yield of heavy (high-boiling) material as a percentage of total product, relative to the reaction temperature of each test, for catalysts of the invention and of the prior art. This figure thus indicates the loss of isobutene to heavy product in an isomerization process directed to isobutene reproduction.

FIG. 2 shows the yield of heavy (high boiling) material relative to reaction temperature for processes using the catalysts of both the present invention and the prior art. At temperatures of 290° C. and above, where isomerization to isobutene becomes significant, the present invention avoids the predominant reaction to heavy product of the prior art.

The comparative maximum FOM and corresponding temperatures were as follows, with two data points presented to show a range of operating temperatures:

| | SAPO-11 (Invention) | | Zeolite (Prior Art) | |
| --- | --- | --- | --- | --- |
| FOM | 15.5 | 17.6 | 0.2 | 0.3 |
| Temperature °C. | 288° | 344° | 261° | 291° |

Example IV

The process of the present invention was demonstrated using FAPO-11 and FAPO-31 catalysts for 1-butene production from 2-butene. FAPO catalysts are described earlier in this specification, and the specific catalyst samples used in these tests had the following approximate properties:

| | | FAPO-11 | FAPO-31 |
| --- | --- | --- | --- |
| Composition, mass %: | $Al_2O_3$ | 37.3 | 39.7 |
| | $P_2O_5$ | 57.1 | 50.1 |
| | $Fe_2O_3$ | 5.6 | 10.2 |
| | | 100.0 | 100.0 |

Tests were performed using the feedstock and procedures of Example I, with the exception that conversion to 1-butene with minimum isobutene by-product was achieved at lower temperatures. Results were as follows:

| | FAPO-11 | | | FAPO-31 | | |
| --- | --- | --- | --- | --- | --- | --- |
| Temperature, °C. | 148° | 203° | 260° | 149° | 205° | 260° |
| WHSV 3.1 | 3.6 | 2.9 | 4.1 | 2.7 | 4.4 | |

-continued

| | FAPO-11 | | | FAPO-31 | | |
|---|---|---|---|---|---|---|
| Temperature, °C. | 148° | 203° | 260° | 149° | 205° | 260° |
| Products, mass % | | | | | | |
| $C_3$ and lighter | 0.0 | 0.0 | 0.0 | 0.0 | 0.0 | 0.0 |
| Butanes | 0.5 | 0.5 | 0.5 | 0.6 | 0.5 | 0.6 |
| Isobutene | 0.0 | 0.0 | 1.5 | 0.0 | 0.0 | 0.2 |
| 1-butene | 1.9 | 10.0 | 17.3 | 4.8 | 13.8 | 17.4 |
| 2-butene | 94.1 | 86.4 | 75.9 | 90.1 | 79.0 | 73.6 |
| $C_5$ and heavier | 3.5 | 3.1 | 4.8 | 4.5 | 6.7 | 8.2 |

The yield of 1-butene at reaction temperatures of above 200° is above equilibrium-concentration values. By-product isobutene varies from nil to less than 10% of 1-butene within the ranges shown.

The maximum FOM and corresponding temperatures were as follows, using 1-butene yield as the criterion and designating difficult-to-separate 25 isobutene as a byproduct:

| | FAPO-11 | FAPO-31 |
|---|---|---|
| FOM | 13.0 | 12.7 |
| Temperature, °C. | 260° | 261° |

Example V

Isomerization of 1-pentene to isopentene, as a combination of 2-methyl pentene-1 and 2-methyl pentene-2, was demonstrated over SAPO-11 catalyst. The SAPO-11 catalyst of Example I was extruded with a silica binder and used for pilot-plant testing of pentene conversion and product selectivity. The feedstock was a mixture of 1-pentene and isopentane containing about 38 mass % pentene. Hydrogen was present at a molar ratio to 1-pentene of about 8. Reactor pressure was about 18 atmospheres, and temperature was varied between 327° and 357° C. After a 50-hour line-out period, pentene conversion averaged about 70% and molar yields from converted pentene were as follows:

| | |
|---|---|
| $C_3$ and lighter | 0.3 |
| Butenes/butanes | 1.8 |
| Isopentenes | 93.4 |
| $C_6$ and heavier | 4.6 |

Figure 3:
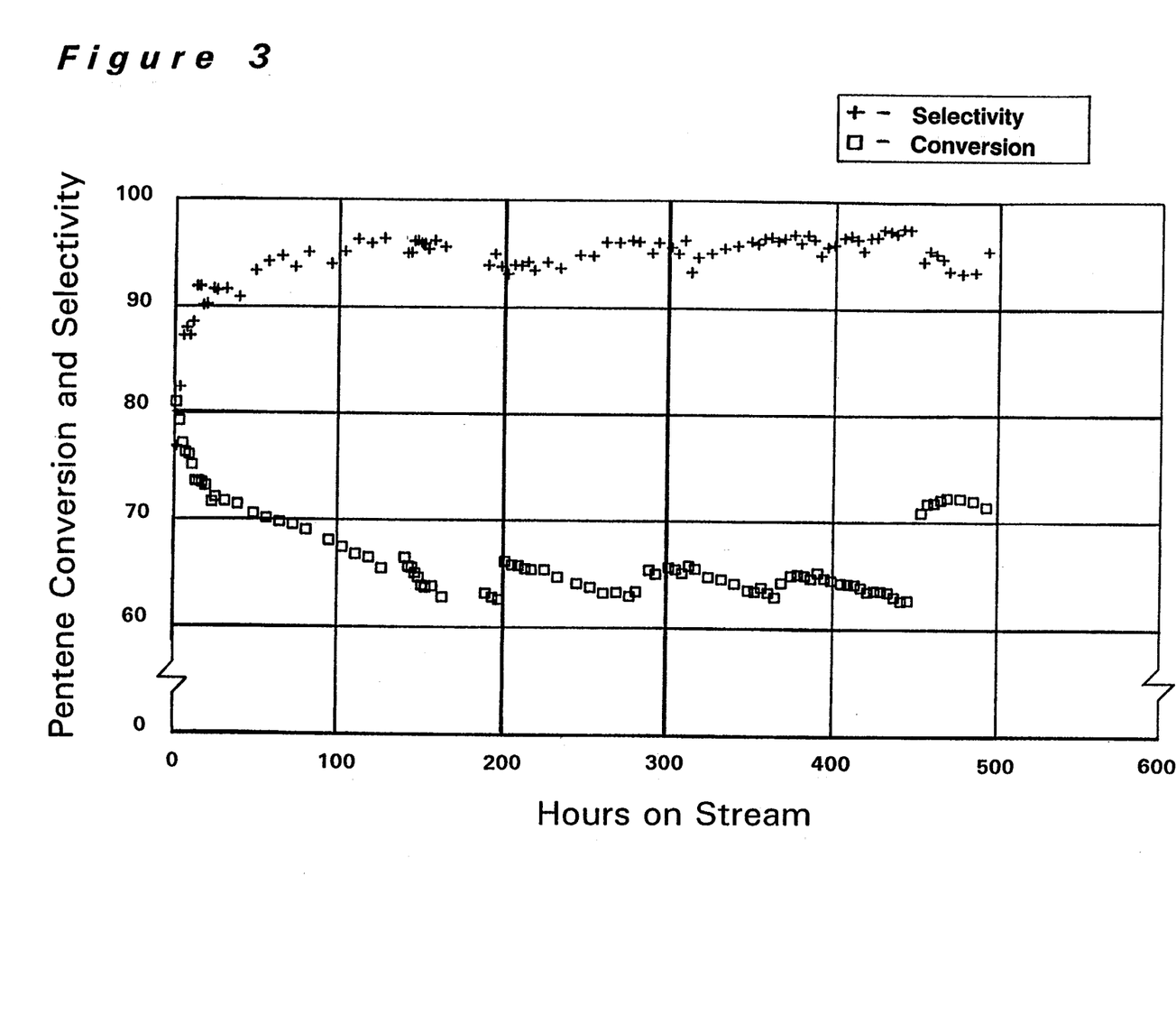
FIG. 3 shows conversion and selectivity for the isomerization of 1-pentene to isopentenes over a period of about 480 hours.

The pilot-plant run was maintained over a period of about 480 hours in order to establish catalyst stability. The results of the extended run are plotted in FIG. 3.

Example VI

Further pilot-plant tests were performed on the Example V feedstock mixture of 1-pentene and isopentane, using the same bound SAPO-11 catalyst, in order to assess the effect of operating temperature on conversion and selectivity. Operating pressure was about 10 atmospheres, and temperatures assessed were 327° and 427° C. Pentene conversion and molar yields from converted pentene were as follows:

| Temperature, °C | 427° | 327° |
|---|---|---|
| Conversion, % | 68.7 | 64.4 |
| Selectivity, mol % | | |
| $C_3$ and lighter | 2.2 | 0.2 |
| Butenes/butanes | 2.2 | 0.8 |
| Isopentenes | 91.5 | 94.6 |

-continued

| Temperature, °C | 427° | 327° |
|---|---|---|
| $C_6$ and heavier | 3.3 | 2.1 |

Example VII

Figure 4:
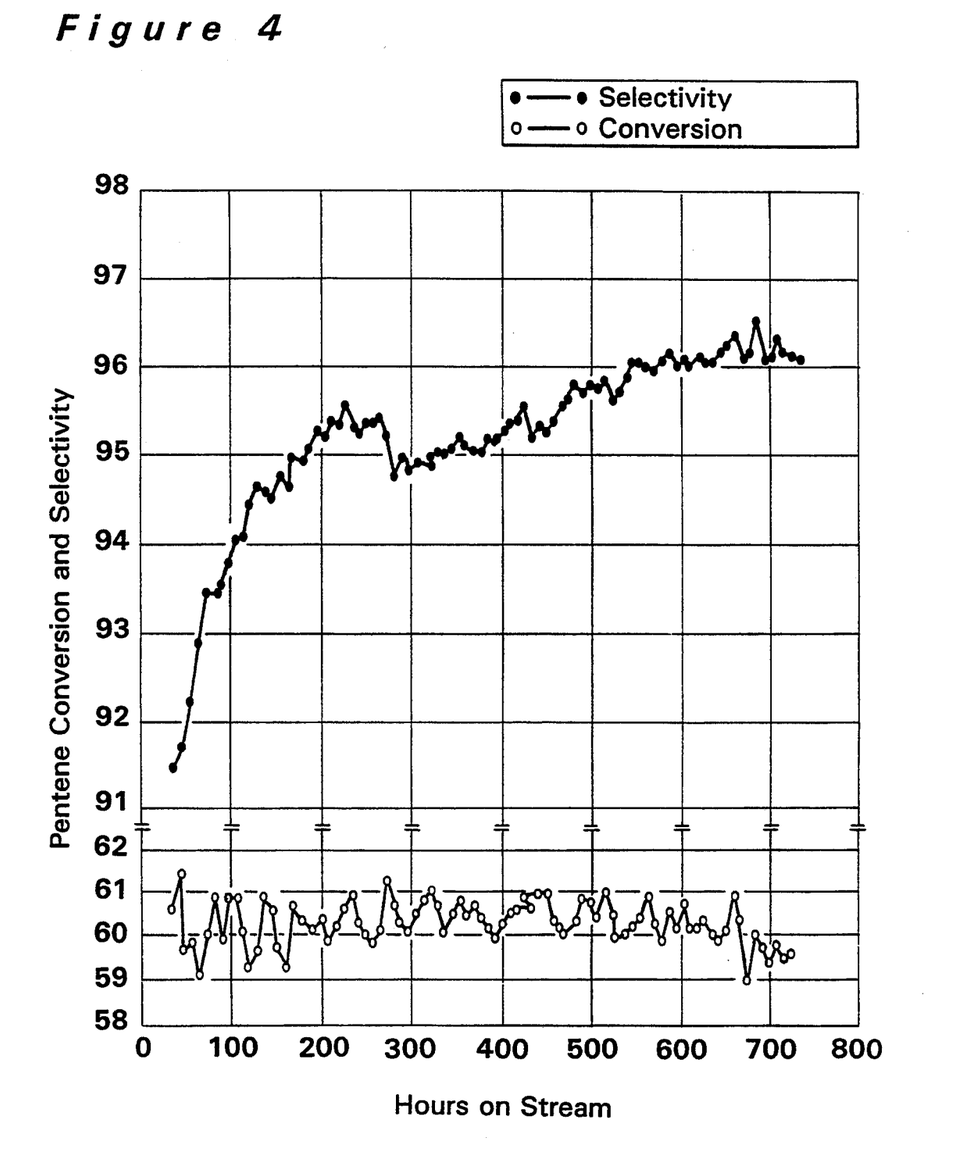
FIG. 4 shows conversion and selectivity for the isomerization of 1-pentene to isopentenes over a period of about 720 hours in the absence of hydrogen.

Isomerization of 1-pentene to isopentene in the substantial absence of hydrogen was demonstrated in a pilot plant over the SAPO-11 catalyst of Example V. The feedstock was a mixture of 1-pentene and normal pentane containing about 27 mass % pentene. Nitrogen was used in place of hydrogen to pressure the pilot plant to a pressure of about 8 atmospheres. Temperature was varied between about 265° and 380° C. during the run. After a line-out period, a stable operation was achieved at a pentene conversion about 60% and isopentene selectivity of 95–96 mass %. The molar ratio of hydrogen to $C_5$ hydrocarbons declined from about 0.003 during the initial period to about 0.001 after two weeks. The pilot-plant run was maintained over a period of over 700 hours in order to establish catalyst stability. The results of the extended run are plotted in FIG. 4.

We claim:

1. A process for the isomerization of pentenes which comprises contacting a pentene-containing feedstock at isomerization conditions in the substantial absence of hydrogen with a catalyst containing at least one non-zeolitic molecular sieve to provide a product containing at least one pentene isomer in greater concentration than in the feedstock.

2. The process of claim 1 wherein the pentene isomer in the product comprises one or more of the isopentenes.

3. The process of claim 1 wherein the isomerization conditions comprise a temperature of from about 200° to 600° C., a pressure of from about atmospheric to 50 atmospheres, and a weight hourly space velocity of from about 0.5 to 100 hr$^{-1}$.

4. The process of claim 1 wherein the non-zeolitic molecular sieve is selected from the group consisting of SAPOs, FAPOs, CoAPSOs, MnAPSOs, MgAPSOs and mixtures thereof.

5. The process of claim 4 wherein the non-zeolitic molecular sieve is selected from the group consisting of SAPO-11, SAPO-31 and SAPO-41.

6. The process of claim 5 wherein the non-zeolitic molecular sieve is SAPO-11.

7. The process of claim 1 wherein the catalyst contains less than 100 mass ppm of Group VIII (8-10) metal.

8. The process of claim 1 wherein the catalyst comprises an inorganic oxide matrix component.

9. The process of claim 8 wherein the inorganic oxide matrix comprises silica.

10. The process of claim 1 wherein the catalyst comprises a halogen component.

11. A process for the skeletal isomerization of pentenes which comprises contacting a feedstock, comprising raffinate pentenes from an etherification process, at isomerization conditions in the substantial absence of hydrogen with a catalyst containing at least one non-zeolitic molecular sieve to provide a product containing a greater concentration of one or more of the isopentenes than in the feedstock.

12.. The process of claim 11 wherein the isomerization conditions comprise a temperature of from about 200° to 600° C., a pressure of from about atmospheric to 50 atmospheres, and a weight hourly space velocity of from about 0.5 to 100 hr$^{-1}$.

13. The process of claim 11 wherein the non-zeolitic molecular sieve is selected from the group consisting of SAPOs, FAPOs, CoAPSOs, MnAPSOs, MgAPSOs and mixtures thereof.

14. The process of claim 13 wherein the non-zeolitic molecular sieve is selected from the group consisting of SAPO-11, SAPO-31 and SAPO-41.

15. The process of claim 14 wherein the catalyst contains less than 100 mass ppm of Group VIII (8-10) metal.

16. The process of claim 11 wherein the catalyst comprises an inorganic oxide matrix component.

17. The process of claim 16 wherein the inorganic oxide matrix comprises silica.

* * * * *